United States Patent
Bryant et al.

(10) Patent No.: US 11,110,226 B2
(45) Date of Patent: *Sep. 7, 2021

(54) SYRINGE

(71) Applicant: NOVARTIS AG, Basel (CH)

(72) Inventors: Andrew Bryant, Reinach (CH);
Heinrich Buettgen, Rheinfelden (CH);
Wolfgang Papst, Eschbach (DE);
Marie Picci, Ranspack-le-bas (FR)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/811,430

(22) Filed: Mar. 6, 2020

(65) Prior Publication Data

US 2020/0214888 A1 Jul. 9, 2020

Related U.S. Application Data

(63) Continuation of application No. 16/409,291, filed on May 10, 2019, which is a continuation of application
(Continued)

(30) Foreign Application Priority Data

Jun. 1, 2012 (EP) .................................... 12170628

(51) Int. Cl.
*A61M 5/31* (2006.01)
*A61M 5/315* (2006.01)
(Continued)

(52) U.S. Cl.
CPC ........ *A61M 5/31513* (2013.01); *A61M 5/001* (2013.01); *A61M 5/28* (2013.01);
(Continued)

(58) Field of Classification Search
CPC .......... A61M 5/31511; A61M 5/31513; A61M 2005/31508; A61M 2005/31516;
(Continued)

(56) References Cited

U.S. PATENT DOCUMENTS

| 1,704,924 A | 3/1929 | Rehm |
|---|---|---|
| 2,236,727 A | 4/1941 | Dewees |

(Continued)

FOREIGN PATENT DOCUMENTS

| CN | 102065939 A | 5/2011 |
|---|---|---|
| DE | 19613035 A1 | 9/1997 |

(Continued)

OTHER PUBLICATIONS

Regeron, Eylea(TM) (aflibercept) Injection for Intravitreal Injection, Nov. 2011, FDA, <<https://www.accessdata.fda.gov/drugsatfda_docs/label/2011/125387lbl.pdf>>. Accessed Dec. 1, 2020 (Year: 2011).*

(Continued)

*Primary Examiner* — William R Carpenter
(74) *Attorney, Agent, or Firm* — Xinsong Xu

(57) ABSTRACT

The invention provides a syringe for use in an ophthalmic injection. The syringe comprises a body, a stopper and a plunger. The body comprises an outlet at an outlet end and the stopper is arranged within the body such that a front surface of the stopper and the body define a variable volume chamber from which a fluid can be expelled though the outlet. The plunger comprises a plunger contact surface at a first end and a rod extends between the plunger contact surface and a rear portion. The plunger contact surface is arranged to contact the stopper but not couple thereto, such that the plunger can be used to force the stopper towards the (Continued)

Figure 1:
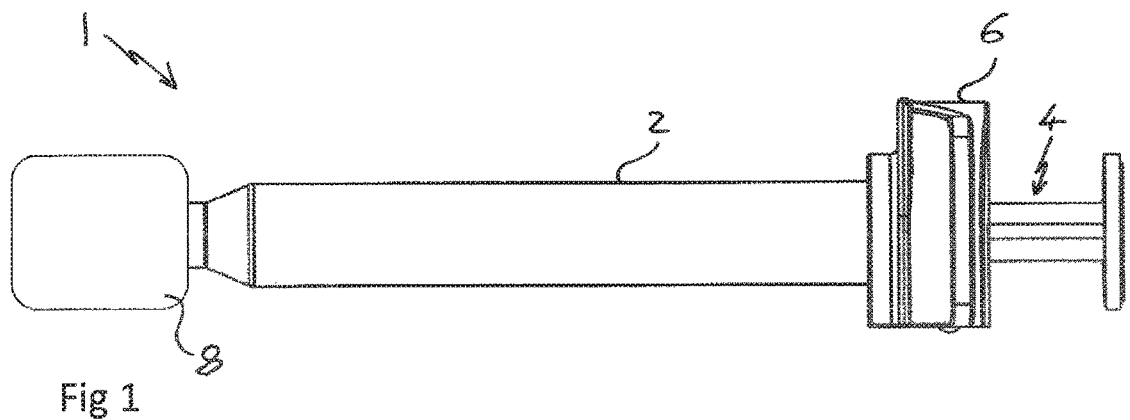

outlet end of the body, reducing the volume of the variable volume chamber, but not to move the stopper away from the outlet end.

26 Claims, 2 Drawing Sheets

Related U.S. Application Data

No. 14/403,801, filed as application No. PCT/EP2013/061215 on May 30, 2013, now abandoned.

(51) Int. Cl.
  *A61M 5/00* (2006.01)
  *A61M 5/28* (2006.01)
  *A61P 27/02* (2006.01)
  *A61F 9/00* (2006.01)

(52) U.S. Cl.
  CPC ......... *A61M 5/31505* (2013.01); *A61P 27/02* (2018.01); *A61F 9/0017* (2013.01); *A61M 5/3137* (2013.01); *A61M 2005/3104* (2013.01); *A61M 2005/3139* (2013.01); *A61M 2005/31508* (2013.01); *Y10T 29/49826* (2015.01)

(58) Field of Classification Search
  CPC .............. A61M 5/31515; A61M 5/315; A61M 5/5013; A61M 5/502
  See application file for complete search history.

(56) References Cited

U.S. PATENT DOCUMENTS

| | | | |
|---|---|---|---|
| 3,148,772 | A | 9/1964 | Saffir |
| 3,248,950 | A | 5/1966 | Pursell |
| 4,252,118 | A | 2/1981 | Richard et al. |
| 4,946,441 | A | 8/1990 | Laderoute |
| 5,181,918 | A | 1/1993 | Brandhorst et al. |
| 5,607,400 | A | 3/1997 | Thibault et al. |
| 5,795,337 | A | 8/1998 | Grimard |
| 7,060,269 | B1 | 6/2006 | Baca et al. |
| 7,077,826 | B1 | 7/2006 | Gray |
| 7,404,278 | B2 | 7/2008 | Wittland et al. |
| 8,075,535 | B2 | 12/2011 | Carrel |
| 9,220,631 | B2 | 12/2015 | Sigg et al. |
| 9,561,329 | B2 | 2/2017 | Kawamura |
| 2001/0056264 | A1 | 12/2001 | Sayama et al. |
| 2002/0065239 | A1* | 5/2002 | Caplan ............... A61K 38/45 514/44 R |
| 2003/0003014 | A1 | 1/2003 | Metzner et al. |
| 2004/0099994 | A1 | 5/2004 | Brinkhues |
| 2005/0010175 | A1* | 1/2005 | Beedon ............... A61M 5/31511 604/218 |
| 2005/0182370 | A1 | 8/2005 | Hato |
| 2006/0264967 | A1 | 11/2006 | Ferreyro et al. |
| 2006/0293270 | A1 | 12/2006 | Adamis et al. |
| 2007/0185496 | A1 | 8/2007 | Beckman et al. |
| 2007/0190058 | A1* | 8/2007 | Shams ............... A61K 9/0048 424/145.1 |
| 2007/0250017 | A1* | 10/2007 | Carred ............... A61M 5/31501 604/220 |
| 2008/0082055 | A1 | 4/2008 | Lloyd et al. |
| 2008/0114306 | A1 | 5/2008 | Bare |
| 2008/0312607 | A1 | 12/2008 | Delmotte et al. |
| 2009/0326458 | A1* | 12/2009 | Chong ............... A61M 5/14248 604/152 |
| 2010/0087796 | A1 | 4/2010 | Baggs |
| 2010/0093648 | A1 | 4/2010 | Cruz |
| 2010/0288393 | A1 | 11/2010 | Malmstrom et al. |
| 2011/0190709 | A1 | 8/2011 | Mitsuno et al. |
| 2011/0276005 | A1 | 11/2011 | Hioki et al. |
| 2012/0078219 | A1 | 3/2012 | Preis |
| 2012/0091026 | A1 | 4/2012 | Chacornac et al. |
| 2012/0271245 | A1 | 10/2012 | Achan, Jr. |
| 2019/0365565 | A1 | 12/2019 | Bryant et al. |
| 2020/0179167 | A1 | 6/2020 | Bryant et al. |

FOREIGN PATENT DOCUMENTS

| | | |
|---|---|---|
| DE | 102008005938 A1 | 7/2009 |
| EP | 1192966 A1 | 4/2002 |
| EP | 1488818 A1 | 12/2004 |
| EP | 2298392 A1 | 3/2011 |
| FR | 2 855 413 A1 | 12/2004 |
| JP | 8-317975 A | 12/1996 |
| JP | 2000-14779 A | 1/2000 |
| JP | 2003-265607 A | 9/2003 |
| JP | 2004-313369 A | 11/2004 |
| JP | 2004313369 A | 11/2004 |
| JP | 2006-016053 A | 1/2006 |
| JP | 2006-528044 A | 12/2006 |
| JP | 2007-014619 A | 1/2007 |
| JP | 2009-508593 A | 3/2009 |
| WO | 2004/091700 A1 | 10/2004 |
| WO | 2007/035621 A1 | 3/2007 |
| WO | 2007/149334 A2 | 12/2007 |
| WO | 2008/077155 A1 | 6/2008 |
| WO | 2009/030976 A1 | 3/2009 |
| WO | 2009/154107 A1 | 12/2009 |
| WO | 2010/081838 A2 | 7/2010 |
| WO | 2011/006877 A1 | 1/2011 |
| WO | 2011/122574 A1 | 10/2011 |
| WO | 2011/125475 A1 | 10/2011 |

OTHER PUBLICATIONS

Vietnamese Office Action dated Sep. 9, 2019, issued in Vietnamese patent application No. 1-2014-03899, filed May 30, 2013.
Hultman C. et al.: "The Physical Chemistry of Decontamination with Gaseous Hydrogen Peroxide", Pharmaceutical Engineering, The Official Magazine of ISPE, Jan./Feb. 2007, vol. 27, No. 1, pp. 1-6.
Carter, P. et al.: "The lowdown on low temperature sterilization for packaged devices", Healthcare Purchasing News (www.hpnonline.com), Self-Study Series, Jul. 2008, pp. 42-45.
Shah, B. D. et al.: "Pre-Filled Syringes: A New Concept", Pharma Bio World (www.pharmabioworld.com), Aug. 2009, pp. 51-57.
Fries, Arno: "Drug Delivery of Sensitive Biopharmaceuticals With Prefilled Syringes", Drug Delivery Technology, May 2009, vol. 9, No. 5, pp. 22-27.
Abdelkader, K. et al.: "Sterile Prefilled Syringes: Market Dynamics and Current Issues in Manufacturing and Quality Control", Baxter, OndrugDelivery Ltd., Copyright 2005, pp. 1-28.
Penn, J.S.et al: "Vascular Endothelial Growth Factor in Eye Disease", available in PMC Jun. 14, 2013, published in Final edited form as: Prog Retin Eye Res. 27(4): 331-371 (2008) (90 pages).
Meyer, C. et al.: "Steps for a Safe Intravitreal Injection Technique—A look at how European and American approaches compare", Retinal Physician, Issue: Jul./Aug. 2009, pp. 1-6.
Sassalos, T. et al., "Prefilled syringes for intravitreal drug delivery," Clin Opthalmol., Apr. 2019, 13:701-706.
Storey, P. et al., "The Impact of Prefilled Syringes on Endophthalmitis Following Intravitreal Injection of Ranibizumab," Am J Ophthalmol. Mar. 2019, 199:200-208.
Petition for Inter Partes Review: *Regeneron Pharmaceuticals, Inc. v. Novartis Pharma AG*, Novartis Technology LLC, Novartis Pharmaceuticals Corporation for U.S. Pat. No. 9,220,631, submitted Jul. 16, 2020 (77 pages).
Kim, L et al., "A brief history of anti-VEGF for the treatment of ocular angiogenesis," Am J Pathol., Aug. 2012, 181 (2):376-9.
Badkar, A. et al., "Development of biotechnology products in pre-filled syringes: technical considerations and approaches," AAPS PharmSciTech. Jun. 12, 2011(2):564-72.
Liu, L et al., "Silicone oil microdroplets and protein aggregates in repackaged bevacizumab and ranibizumab: effects of long-term storage and product mishandling," Invest Ophthalmol Vis Sci. 2011, 52(2):1023-34.

(56) References Cited

OTHER PUBLICATIONS

Lambert, B. et al., "Radiation and ethylene oxide terminal sterilization experiences with drug eluting stent products," AAPS PharmSciTech. 2011, 12(4):1116-26.

Kereluk, K. et al., "Microbiological aspects of ethylene oxide sterization. I. Experimental apparatus and methods," Appl Microbiol. 1970, 19(1):146-51.

Leventon, W. "Medical Device Sterilization: What Manufacturers Need to Know," published Sep. 1, 2002, available at <https://www.mddionline.com/news/medical-device-sterilization-what-manufacturers-need-know>, retrieved on Sep. 23, 2020 (13 pages).

U.S. Department of Health and Human Services, FDA, CDER, CBER, "Guidance for Industry: Container Closure Systems for Parking Human Drugs and Biologics," May 1999 (56 pages).

U.S. Department of Health and Human Services, FDA, CDER, CBER, "Guidance for Industry: Sterile Drug Products Produced by Aseptic Processing—Current Good Manufacturing Practice," Sep. 2004 (63 pages).

Office Action issued in Japanese Patent Application No. 2020-043041, dated Jan. 5, 2021. (English Machine Translation attached).

English Translation of Office Action issued in Korean Patent Application No. 10-2020-7035156, dated Jan. 5, 2021.

Jurgen, S., "FR B002 0.5MG/0.05ML Liquid in (pre-filled) syringe", PFS Development Report, Novartis, (2013), pp. 1-5.

Somner et al.: Inadvertent injections of Intravitreal Air During Intravitreal Lucentis Injection for Wet Age-Related Macular Degeneration: An Undescribed Complication, Oct. 3, 2008, Eye 23, 1744; doi 10.1038/ eye.2008.297 (Year 2008).

Genetech, Inc., Highlights of Prescribing Information, LUCENTIS [ranibizumab injection], Intravitreal Injection, (Year 2006), STN BLA 12516/053, pp. 5-11.

Third Party Observation for application No. EP20156274, submission of observation took place on Nov. 26, 2020, Title: SYRINGE, Publication Number: EP3679922, Applicant: NOVARTIS AG[CH], Date fo publication: Jul. 15, 2020, Date of filing: May 30, 2013, 94 pages.

Third Party Observation filed by Anonymous for application No. EP20200198921 dated Apr. 14, 2021, 5 pages.

Relevance of Third-Party Observation dated Nov. 26, 2021 considered not relevant by Examiner Jun. 21, 2021, 2 pages.

Extended European Search Report for Application No. 21164847.2 dated Jul. 1, 2021, 8 pages.

Third Party Observation filed by Anonymous for Application No. JP2020-043041 dated Apr. 27, 2021,22 pages (English Translation attached).

Third Party Observation filed by Anonymous for Application No. JP2020-043041 dated May 6, 2021, 30 pages (English Translation attached).

Regeneron Pharmaceuticals, Inc., "Bayer and Regeneron Report Positive Top-Line Results of Two Phase 3 Studies With Vegf Trap-Eye in Wet Age-Related Macular Degeneration," Nov. 22, 2010, 5 pages (submitted as document 2-3 in Third Party Observation for Application No. JP2020-043041 dated May 3, 2021).

Highlights of Prescribing Information, Magugen (pegaptanib sodium injection), NDA21-759/S-018, 10 pages (submitted as document 2-5 in Third Party Observation for Application No. JP2020-043041 dated May 6, 2021).

* cited by examiner

SYRINGE

CROSS REFERENCE TO RELATED APPLICATIONS

This application claims priority to and is a continuation of U.S. application Ser. No. 16/409,291, filed May 10, 2019, which claims priority to and is a continuation of U.S. application Ser. No. 14/403,801, filed Nov. 25, 2014, which is a national stage entry of PCT/EP2013/061215, filed May 30, 2013, which claims priority to EP Appln. No. 12170628.7, filed Jun. 1, 2012. All of the above are hereby incorporated into this application by reference in their entirety.

The present invention relates to a syringe, particularly to a small volume syringe such as a syringe suitable for ophthalmic injections. The invention also extends to a method of assembling such a syringe.

Many medicaments are delivered to a patient in a syringe from which the user can dispense the medicament. If medicament is delivered to a patient in a syringe it is often to enable the patient, or a caregiver, to inject the medicament. It is important for patient safety and medicament integrity that the syringe and the contents of that syringe are sufficiently sterile to avoid infection, or other, risks for patients. Sterilisation can be achieved by terminal sterilisation in which the assembled product, typically already in its associated packaging, is sterilised using heat or a sterilising gas.

For small volume syringes, for example those for injections into the eye in which it is intended that less than about 0.1 ml of liquid is to be injected, the sterilisation can pose difficulties that are not necessarily associated with larger syringes. Changes in pressure, internal or external to the syringe, can cause parts of the syringe to move unpredictably, which may alter sealing characteristics and potentially compromise sterility. Incorrect handling, including assembly, of the syringe can also pose risks to product sterility.

The present invention provides a syringe, the syringe comprising a body, a stopper and a plunger, the body comprising an outlet at an outlet end and the stopper being arranged within the body such that a front surface of the stopper and the body define a variable volume chamber from which a fluid can be expelled though the outlet, the plunger comprising a plunger contact surface at a first end and a rod extending between the plunger contact surface and a rear portion, the plunger contact surface arranged to contact the stopper but not couple thereto, such that the plunger can be used to force the stopper towards the outlet end of the body, reducing the volume of the variable volume chamber, but not to move the stopper away from the outlet end.

Providing a plunger which does not couple to the stopper reduces the chances for incorrect handling of the syringe as the plunger can be withdrawn from the syringe without movement of the stopper away from the outlet end. This prevents a user from accidentally moving the plunger (and therefore a stopper connected thereto) and causing non-sterile air (or other fluid) to be drawn into the syringe, or causing movement of the stopper to a non-sterile area. It has also been found that creating a connection between a plunger to a stopper during assembly, using for example a screwing action or a push-fit action, can distort the stopper in an unpredictable manner which may compromise the sealing and/or sterility of the final product, or may increase pressure in the variable volume chamber which could cause fluid leakage from the outlet end.

The body of the syringe may be a substantially cylindrical shell, or may include a substantially cylindrical bore with a non-circular outer shape. The outlet end of the body includes an outlet through which a fluid housed within the variable volume chamber can be expelled as the volume of said chamber is reduced. The outlet may comprise a projection from the outlet end through which extends a channel having a smaller diameter than that of the variable volume chamber. The outlet may be adapted, for example via a luer lock type connection, for connection to a needle or other accessory such as a sealing device which is able to seal the variable volume chamber, but can be operated, or removed, to unseal the variable chamber and allow connection of the syringe to another accessory, such as a needle. Such a connection may be made directly between the syringe and accessory, or via the sealing device. The body extends along a first axis from the outlet end to a rear end.

The body may be made from a plastic material or from glass, or from any other suitable material and may include indicia on a surface thereof to act as an injection guide.

The stopper may be made from rubber, silicone or other suitable resiliently deformable material. The stopper provides a sealing function by defining the rear of the variable volume chamber with a fluid tight seal which also provides a sterility seal. The stopper may be substantially cylindrical and the stopper may include one or more circumferential ribs around an outer surface of the stopper, the stopper and ribs being dimensioned such that the ribs form a substantially fluid tight seal with an internal surface of the syringe body. The front surface of the stopper may be any suitable shape, for example substantially planar, or substantially conical. The stopper may be substantially solid or may include recesses. The rear surface of the stopper may include a substantially central recess which may be any shape provided the sealing function of the stopper is not compromised. Said central recess may be substantially cylindrical in shape or said central recess may include an initial bore having a first diameter, the initial bore leading from the rear surface into the stopper to an inner recess having a second diameter, the second diameter being larger than the first diameter. Such a central recess could be used to connect a plunger to the stopper using a snap fit feature in a known manner. Such a design allows a substantially standard stopper design to be used and this can reduce the parts cost for the syringe. Also, it is noted that removing material from the central portion of the stopper, where it is not needed for the stopper to function as required, reduces the stopper weight and reduces the amount of material needed to manufacture the stopper. The stopper may be substantially rotationally symmetric about an axis through the stopper.

The plunger comprises a plunger contact surface and extending from that a rod extends from the plunger contact surface to a rear portion. The rear portion may include a user contact portion adapted to be contacted by a user during an injection event. The user contact portion may comprise a substantially disc shaped portion, the radius of the disc extending substantially perpendicular to the axis along which the rod extends. The user contact portion could be any suitable shape. The axis along which the rod extends may be the first axis, or may be substantially parallel with the first axis.

The plunger contact surface is adapted to make contact with the rear surface of the stopper, but not couple thereto. The plunger contact surface may be substantially planar and may be substantially circular in shape. The plunger contact surface may be substantially circular with an outer diameter less than the internal diameter of the body. The diameter of the plunger contact surface may be substantially equal to the diameter of the rear surface of the stopper with which it is to make contact. The plunger contact surface may be adapted to present a substantially rotationally symmetrical surface to the rear surface of the stopper as this assists in providing a repeatable and evenly distributed force to the stopper during use which can help to prevent distortions. The plunger contact surface may not be planar and may comprise an annular contact surface to contact the stopper at or adjacent an out edge thereof. The plunger contact surface may comprise a plurality of arms which extend from the plunger rod to make contact with the stopper. The plunger contact surface may be substantially rotationally symmetrical in any of the above, or other, embodiments.

The rod may have a round or cross-form cross-section. A cross-form cross section may be formed from ribs extending along at least part of the rod. The ribs may extend substantially parallel with the axis along which the rod extends. The cross-form cross section provides rigidity to the rod without significantly increasing manufacturing complexity.

The rod may be manufactured from any suitable material, or combination of materials, and in one embodiment is made from a plastic material. The rod may be substantially rigid under expected use conditions. Although some flexing of the materials in the plunger is unavoidable in a bulk manufactured product, it is advantageous that the rod cannot flex significantly during use, particularly for low volume, accurate, injections as any flexing could lead to unpredictable dosing results.

The syringe may include a backstop arranged at a rear portion of the body. The backstop may be removable from the syringe. If the syringe body includes terminal flanges at the end opposite the outlet end the backstop may be configured to substantially sandwich terminal flanges of the body as this prevent movement of the backstop in a direction parallel to the first axis.

The rod may comprise at least one rod shoulder directed away from the outlet end and the backstop may include a backstop shoulder directed towards the outlet end to cooperate with the rod shoulder to substantially prevent movement of the rod away from the outlet end when the backstop shoulder and rod shoulder are in contact. Restriction of the movement of the rod away from the outlet end can help to maintain sterility during terminal sterilisation operations, or other operations in which the pressure within the variable volume chamber or outside the chamber may change. During such operations any gas trapped within the variable volume chamber, or bubbles that may form in a liquid therein, may change in volume and thereby cause the stopper to move. Movement of the stopper away from the outlet could result in the breaching of a sterility zone created by the stopper. This is particularly important for low volume syringes where there are much lower tolerances in the component sizes and less flexibility in the stopper. The term sterility zone as used herein is used to refer to the area within the syringe that is sealed by the stopper from access from either end of the syringe. This may be the area between a seal of the stopper, for example a circumferential ridge, closest to the outlet and a seal of the stopper, for example a circumferential ridge, furthest from the outlet. The distance between these two seals defines the sterility zone of the stopper since the stopper is installed into the syringe barrel in a sterile environment.

As noted above, a terminal sterilisation process may be used to sterilise the complete article and such a process may use a known process such as an Ethylene Oxide or a Hydrogen Peroxide sterilisation process.

The inclusion of one or more circumferential ribs on the stopper can alter the force required to cause the stopper to move from a stationary position and can also alter the sealing properties of the stopper. To further assist in maintaining sterility during the operations noted above the stopper may comprise at least a front circumferential rib and a rear circumferential rib and those ribs may be separated in a direction along the first axis by at least 3 mm, by at least 3.5 mm, by at least 3.75 mm or by 4 mm or more. One or more additional ribs (for example 2, 3, 4 or 5 additional ribs, or between 1-10, 2-8, 3-6 or 4-5 additional ribs) may be arranged between the front and rear ribs. In one embodiment there are a total of three circumferential ribs.

A stopper with such an enhanced sterility zone can also provide protection for the injectable medicament during a terminal sterilisation process. Some medicaments, example a biological medicament, could be damaged by exposure to Ethylene Oxide. More ribs on the stopper, or a greater distance between the front and rear ribs, can reduce the potential exposure of the medicament to the sterilising agent.

The rod shoulder may be arranged within the external diameter of the rod, or may be arranged outside the external diameter of the rod. By providing a shoulder that extends beyond the external diameter of the rod, but still fits within the body, the shoulder can help to stabilise the movement of the rod within the body by reducing movement of the rod perpendicular to the first axis. The rod shoulder may comprise any suitable shoulder forming elements on the rod, but in one embodiment the rod shoulder comprises a substantially disc shaped portion on the rod.

In one embodiment of the syringe, when arranged with the plunger contact surface in contact with the stopper and the variable volume chamber is at its intended maximum volume there is a clearance of no more than about 2 mm between the rod shoulder and backstop shoulder. In some embodiments there is a clearance of less than about 1.5 mm and in some less than about 1 mm. This distance is selected to substantially limit or prevent excessive rearward (away from the outlet end) movement of the stopper.

In one embodiment the variable volume chamber has an internal diameter greater than 5 mm or 6 mm and less than 3 mm or 4 mm. The internal diameter may be between 3 mm and 6 mm, or between 4 mm and 5 mm. In another embodiment the syringe is dimensioned so as to have a nominal maximum fill volume of volume of between about 0.25 ml and 0.75 ml, or between 0.4 ml and 0.6 ml. The length of the body of the syringe may be less than 70 mm, less than 60 mm or less than 50 mm. In one embodiment the length of the syringe body is between 45 mm and 50 mm, the internal diameter is between 4 mm and 5 mm and the fill volume is between 0.1 ml and 0.3 ml of liquid.

In one embodiment, the syringe is suitable for ophthalmic injections, and as such has a suitably small volume. The syringe may be adapted for ophthalmic injections. The syringe may also be silicone free, or substantially silicone free, or may comprise a low level of silicone as lubricant. In one embodiment, the syringe may meet USP789.

The variable volume chamber of the syringe may be filled with any suitable injectable liquid or medication, for example an injectable medicament. In one embodiment the variable volume chamber is filled with an injectable medicament comprising an active suitable for the treatment of an ocular disease. Examples of such ocular diseases include choroidal neovascularisation, age-related macular degeneration (both wet and dry forms), macular edema secondary to retinal vein occlusion (RVO) including both branch RVO (bRVO) and central RVO (cRVO), choroidal neovascularisation secondary to pathologic myopia (PM), diabetic macular edema (DME), diabetic retinopathy, and proliferative retinopathy. In one embodiment, the medicament comprises a biologic active. The biologic active may be an antibody (or fragment thereof) or a non-antibody protein. In one embodiment the medicament comprises a VEGF antagonist. Suitable VEGF antagonists include ranibizumab (Lucentis™), bevacizumab (Avastin™), aflibercept (Eylea™, also known as VEGF-Trap Eye), conbercept (KH902 from Chengdu Kanghong Biotechnologies Co. Ltd, described as FP3 in WO2005/121176, the contents of which are hereby incorporated by reference) and the related glycoform KH906 or pazopanib (from GlaxoSmithKline).

In one embodiment, the syringe is filled with between about 0.01 ml and about 2 ml (for example between about 0.05 ml and about 1 ml, between about 0.1 ml and about 0.5 ml) of an injectable medicament. Of course, typically a syringe is filled with more than the desired dose to be administered to the patient, to take into account wastage due to "dead space" within the syringe and needle. Thus, in one embodiment, the syringe is filled with a dosage volume (i.e. the volume of medicament intended for delivery to the patent) of between about 0.01 ml and about 2 ml (e.g. between about 0.05 ml and about 1 ml, between about 0.1 ml and about 0.5 ml) of an injectable medicament. For example, for Lucentis, the dosage volume is 0.05 ml or 0.03 ml (0.5 mg or 0.3 mg) of a 10 mg/ml injectable medicament solution; for Eylea, the dosage volume is 0.05 ml of a 40 mg/ml injectable medicament solution.

As noted above, when the syringe contains a medicament solution the outlet may be reversibly sealed to maintain sterility of the medicament. This sealing may be achieved through the use of a sealing device as is known in the art. For example the OVS™ system which is available from Vetter Pharma International GmbH. The sealing of the outlet should be such that that sterility of the contents of the variable volume chamber can be maintained until such time as the stopper is moved to breach the sterility seal or the outlet is unsealed.

By providing a plunger that does not couple with the stopper a new method of assembly is made possible and so the invention further provides a method of assembling a syringe, the method comprising the steps of:
i) providing a body and a stopper, the body comprising an outlet at an outlet end and the stopper being arranged within the body such that a front surface of the stopper and the body define a variable volume chamber from which a fluid can be expelled though the outlet, the outlet being releasably sealed and the variable volume chamber containing a medicament; and
ii) providing a plunger comprising a plunger contact surface at a first end and a rod extending between the plunger contact surface and a rear portion and arranging the plunger contact surface and at least part of the plunger within the body without coupling the plunger to the stopper.

The method may further comprise an additional step, step iii), of filling the variable volume chamber of the syringe, which may be filled with any suitable injectable medicament. In one embodiment the variable volume chamber is filled with an injectable medicament suitable for the treatment of an ocular disease. Examples of such ocular diseases include choroidal neovascularisation, age-related macular degeneration (both wet and dry forms), macular edema secondary to retinal vein occlusion (RVO) including both branch RVO (bRVO) and central RVO (cRVO), choroidal neovascularisation secondary to pathologic myopia (PM), diabetic macular edema (DME), diabetic retinopathy, and proliferative retinopathy. In one embodiment, the medicament comprises a biologic active. The biologic active may be an antibody (or fragment thereof) or a non-antibody protein. In one embodiment the medicament comprises a VEGF antagonist. Suitable VEGF antagonists include ranibizumab (Lucentis™), bevacizumab (Avastin™), aflibercept (Eylea™, also known as VEGF-Trap Eye), conbercept (KH902 from Chengdu Kanghong Biotechnologies Co. Ltd, described as FP3 in WO2005/121176, the contents of which are hereby incorporated by reference) and the related glycoform KH906 or pazopanib (from GlaxoSmithKline).

It should be noted that steps ii) and iii) above may be carried out in either order. Thus the method may comprise, in sequence, steps i), ii), iii) or steps i), iii), ii) or steps iii), i), ii).

The method may further comprise a step iv) of packaging the assembled syringe in a substantially sealed package. The method may further comprise a terminal sterilisation step, step v), following packaging. The terminal sterilisation step may comprise known techniques such as Ethylene Oxide sterilisation of Hydrogen Peroxide sterilisation.

The invention also extends to a sealed package containing a sterile pre-filled syringe substantially as described herein.

If the rod comprises a rod shoulder as described above and the syringe includes a removable backstop as described the backstop may be coupled to the syringe body after the plunger has been arranged in the body and the rod shoulder is arranged between the outlet end and the backstop shoulder. By ensuring that the rod shoulder is arranged between the outlet end and the backstop shoulder when the backstop is coupled to the device a complex mechanism for enabling the movement of the rod shoulder past the backstop shoulder after coupling the backstop to the syringe is avoided.

In one embodiment step i) and iii) are carried out in a sterile, or substantially sterile, environment. At some point between the filling step and the final assembly being sealed into packaging the syringe is removed from the sterile, or substantially sterile, environment. A terminal sterilisation step can then be conducted on the packaged product.

In one embodiment of the method the plunger rod is dropped into the syringe body. This is a simple operation and makes use of gravity rather than any automated assembly equipment. This is made possible because the rod does not need to be manipulated or forced to couple with the stopper.

The invention also provides a plunger suitable for use in the syringe or method described above.

It should be understood that throughout this specification and in the claims that follow, unless the context requires otherwise, the word "comprise", or variations such as "comprises" or "comprising", implies the inclusion of the stated integer or step, or group of integers or steps. The term "comprising" encompasses "including" as well as "consisting" e.g. a composition "comprising" X may consist exclusively of X or may include something additional e.g. X+Y. It should also be understood that, unless not physically possible, features described in connection with one embodiment can be used alone, or in combination with one or more features described in connection with the same embodiment or one or more other embodiments. The term "about" in relation to a numerical value x is optional and means, for example, x+/−10%.

Figure 2:
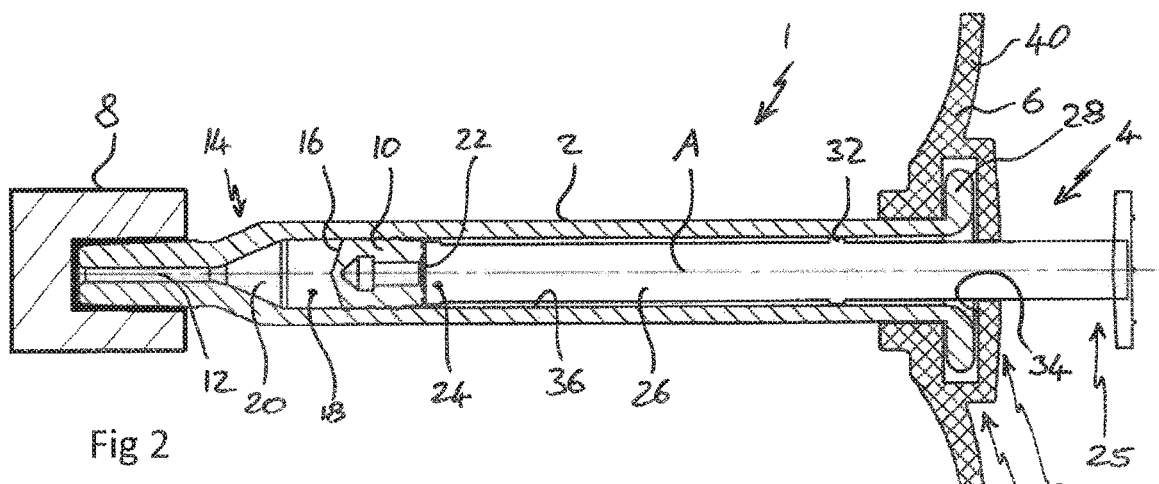
Figure 3:
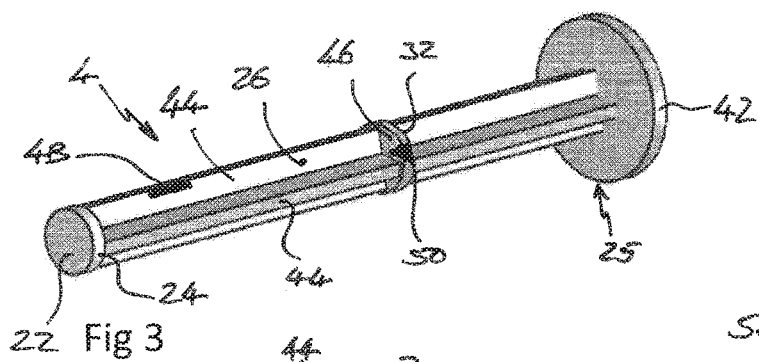
Figure 4:
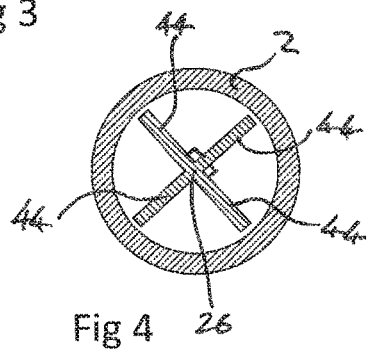
Figure 5:
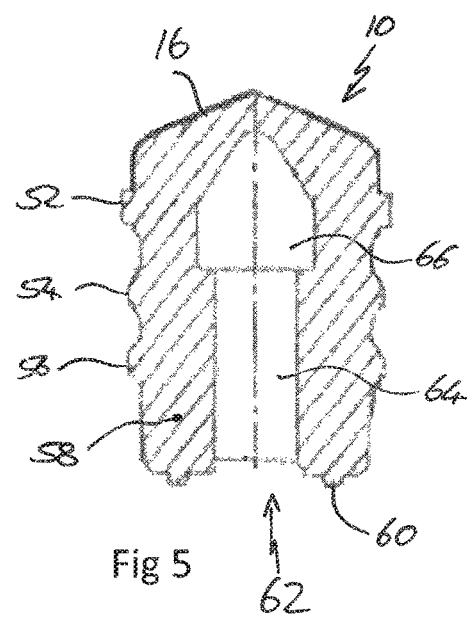
Figure 6:
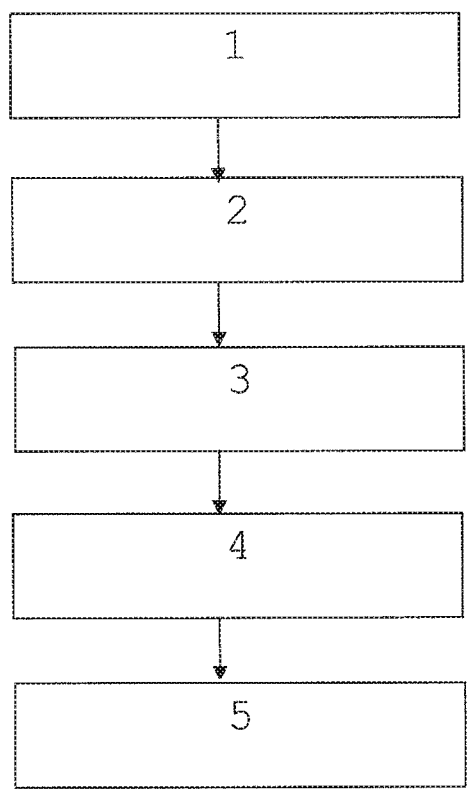

The invention will now be further described, by way of example only, with reference to the following drawings in which:

FIG. 1 shows a side view of a syringe;
FIG. 2 shows a cross section of a top down view of a syringe;
FIG. 3 shows a view of a plunger;
FIG. 4 shows a cross section though a plunger;
FIG. 5 shows a stopper; and
FIG. 6 shows a flowchart of the assembly process.

FIG. 1 shows a view from a side of a syringe 1 comprising a body 2, plunger 4, backstop 6 and a sealing device 8.

FIG. 2 shows a cross section through the syringe 1 of FIG. 1 from above. The syringe 1 is suitable for use in an ophthalmic injection. The syringe 1 comprises a body 2, a stopper 10 and a plunger 4. The syringe 1 extends along a first axis A. The body 2 comprises an outlet 12 at an outlet end 14 and the stopper 10 is arranged within the body 2 such that a front surface 16 of the stopper 10 and the body 2 define a variable volume chamber 18. The variable volume chamber 18 contains an injectable medicament 20 comprising ranibizumab. The injectable fluid 20 can be expelled though the outlet 12 by movement of the stopper 10 towards the outlet end 14 thereby reducing the volume of the variable volume chamber 18. The plunger 4 comprises a plunger contact surface 22 at a first end 24 and a rod 26 extending between the plunger contact surface 22 and a rear portion 25. The plunger contact surface 22 is arranged to contact the stopper 10 but not couple thereto, such that the plunger 4 can be used to move the stopper 10 towards the outlet end 14 of the body 2. Such movement reduces the volume of the variable volume chamber 18 and causes fluid therein to be expelled though the outlet. However, since the plunger 4 is not coupled to the stopper 10 it is not possible to use the plunger 4 to move the stopper 10 away from the outlet end 14.

The backstop 6 is attached to the body 2 by coupling to a terminal flange 28 of the body 2. The backstop 6 includes sandwich portion 30 which is adapted to substantially sandwich at least some of the terminal flange 28 of the body 2. The backstop 6 is adapted to be coupled to the body 2 from the side by leaving one side of the backstop 6 open so that the backstop 6 can be fitted to the syringe 2.

The body 2 defines a substantially cylindrical bore 36 which has a bore radius. The rod 26 comprises a rod shoulder 32 directed away from the outlet end 14. The rod shoulder 32 extends to a rod shoulder radius from the first axis A which is such that it slightly less than the bore radius so that the shoulder fits within the bore 36. The backstop 6 includes a backstop shoulder 34 directed towards the outlet end 14. The shoulders 32,34 are configured to cooperate to substantially prevent movement of the rod 26 away from the outlet end 14 when the backstop shoulder 34 and rod shoulder 32 are in contact. The backstop shoulder 34 extends from outside the bore radius to a radius less than the rod shoulder radius so that the rod shoulder 32 cannot pass the backstop shoulder 34 by moving along the first axis A. In this case the rod shoulder 32 is substantially disc, or ring, shaped and the backstop shoulder 34 includes an arc around a rear end 38 of the body 2.

The backstop 6 also includes two finger projections 40 which extend in opposite directions away from the body 2 substantially perpendicular to the first axis A to facilitate manual handling of the syringe 1 during use.

In this example the syringe comprises a 0.5 ml body 2, that is a body with a notional maximum fill volume of about 0.5 ml, filled with between about 0.1 and 0.3 ml of an injectable medicament 20 comprising a 10 mg/ml injectable solution comprising ranibizumab. The syringe body 2 has an internal diameter of about between about 4.5 mm and 4.8 mm, a length of between about 45 mm and 50 mm.

The plunger 4 and stopper 10 will be described in more detail with reference to later figures.

FIG. 3 shows a perspective view of the plunger 4 of FIG. 1 showing the plunger contact surface 22 at the first end 24 of the plunger 4. The rod 26 extends from the first end 24 to the rear portion 25. The rear portion 25 includes a disc shaped flange 42 to facilitate user handling of the device. The flange 42 provides a larger surface area for contact by the user than a bare end of the rod 26.

The rod 26 comprises ribs 44 which extend along the rod 26, the ribs forming a cross-form cross section for the rod 26 as shown in more detail in subsequent figures. The rod 26 comprises a disc shaped portion 46, the disc shaped portion 46 extending radially beyond the ribs 44 and also forming the rod shoulder 32.

The ribs 44 may be substantially solid, or may include gaps 48. The disc portion 46 may be solid, or may include gaps 50. Gaps 48,50 may be used to facilitate gas flow within the body 2 if necessary for sterilization, or other, purposes.

FIG. 4 shows a cross section though a syringe body 2 and rod 26. The rod 26 includes four longitudinal ribs 44 and the angle between the ribs is 90°.

FIG. 5 shows a detailed view of a stopper 10 showing a conical shaped front surface 16 and three circumferential ribs 52,54,56 around a substantially cylindrical body 58. The axial gap between the first rib 52 and the last rib 56 is about 3 mm. The rear surface 60 of the stopper 10 includes a substantially central recess 62. The central recess 62 includes an initial bore 64 having a first diameter. The initial bore 64 leading from the rear surface 60 into the stopper 10 to an inner recess 66 having a second diameter, the second diameter being larger than the first diameter.

FIG. 6 shows a flow chart for the assembly of a syringe 1. In Step 1 a prefilled body 2 is provided. The prefilled body comprises a body 2 filled with an injectable medicament 20 comprising ranibizumab, although other medicaments could be used in addition or instead, or a placebo solution could be used. A stopper 10 is arranged in the body 2 to form a variable volume chamber 18 and the outlet 12 is sealed with a sealing device 8.

In Step 2 a plunger 4 is arranged in the body 2. In one embodiment the plunger 4 is dropped into the body 2. This may be by gravity alone, or the plunger may be placed into the body 2 using a machine or human and the body then oriented so that the plunger 4 falls into the body 2 until the plunger contact surface 22 makes contact with the stopper 10.

In Step 3 a backstop 6 is coupled to the terminal flange 28 of the body. The backstop 6 and rod being arranged such that the rod shoulder 32 is located between the outlet end of the body and the backstop shoulder 34.

In Step 4 the syringe is sealed into a package and in Step 5 the package and its contents is sterilised in a terminal sterilisation process. The terminal sterilisation process may use known process such as an Ethylene Oxide or a Hydrogen Peroxide sterilisation process.

It should be understood that the invention has been described above by way of example only and that modifications in detail can be made without departing from the scope of the claims.

The invention claimed is:

1. A packaged, small volume, terminally sterilized syringe, comprising a small volume, terminally sterilized syringe including:
   a body, a stopper, and a plunger,
      wherein the body comprises an outlet at an outlet end and the stopper is arranged within the body such that a front surface of the stopper and the body define a variable volume chamber from which a fluid can be expelled though the outlet,
      wherein the plunger comprises a plunger contact surface at a first end and a rod extending between the plunger contact surface and a rear portion, the plunger contact surface is arranged to contact the stopper but does not couple thereto, such that the plunger can be used to force the stopper towards the outlet end of the body, thereby reducing the volume of the variable volume chamber, but does not to move the stopper away from the outlet end, whereby the syringe is suitable for ophthalmic injection,
      wherein the stopper comprises at least a front circumferential rib and a rear circumferential rib which are separated in a direction along the longitudinal axis of the body to define a sterility zone having a length of at least 3 mm,
      wherein the rod includes at least one rod shoulder directed away from the outlet end and the syringe includes a backstop arranged at a rear portion of the body, the backstop including a backstop shoulder directed towards the outlet end to cooperate with and contact the rod shoulder to limit movement of the plunger away from the outlet end to a distance less than the length of the sterility zone, wherein when the plunger contact surface is in contact with the stopper the backstop shoulder and rod shoulder are not in contact with one another,
      wherein the syringe is dimensioned to have a nominal maximum fill volume of between 0.25 ml and 0.75 ml and the variable volume chamber is filled with 40 mg/ml solution of aflibercept, and the dosage volume is 0.05 ml,
   a sealed package, wherein the small volume, terminally sterilized syringe is enclosed within the sealed package.

2. The syringe according to claim 1, wherein the variable volume chamber has an internal diameter between about 3 mm and about 6 mm.

3. The syringe according to claim 1, wherein the length of the body of the syringe is less than 70 mm.

4. The syringe according to claim 1, which is substantially silicone free.

5. The syringe according to claim 1, wherein the body is made out of plastic or glass.

6. The syringe according to claim 1, which is dimensioned so as to have a nominal maximum volume between about 0.4 ml and about 0.6 ml.

7. The syringe according to claim 6, wherein the nominal maximum volume is about 0.5 ml.

8. The syringe according to claim 1, which has an internal diameter between about 4.5 mm and about 4.8 mm.

9. The syringe according to claim 1, wherein the outlet is reversibly sealed with a sealing device.

10. The syringe of claim 1, wherein the front circumferential rib and the rear circumferential rib are separated in a direction along the longitudinal axis of the body by at least 3.5 mm.

11. The syringe of claim 1, wherein the front circumferential rib and the rear circumferential rib are separated in a direction along the longitudinal axis of the body by at least 3.75 mm.

12. The syringe of claim 1, wherein the front circumferential rib and the rear circumferential rib are separated in a direction along the longitudinal axis of the body by at least 4 mm.

13. The syringe of claim 1, which comprises a total of three circumferential ribs.

14. The syringe of claim 1, which further comprises one or more additional circumferential ribs arranged between the front circumferential rib and the rear circumferential rib.

15. The syringe of claim 14, which further comprises two or more additional circumferential ribs.

16. A method of assembling a packaged, small volume, terminally sterilized syringe, the method comprising:
   a. providing a body and a stopper, wherein the body comprises an outlet at an outlet end and the stopper is arranged within the body such that a front surface of the stopper and the body define a variable volume chamber from which a fluid can be expelled though the outlet, and wherein the outlet is releasably sealed and the variable volume chamber contains a medicament, wherein the stopper comprises at least a front circumferential rib and a rear circumferential rib which are separated in a direction along the longitudinal axis of the body to define a sterility zone having a length of at least 3 mm; and
   b. providing a plunger comprising a plunger contact surface at a first end and a rod extending between the plunger contact surface and a rear portion and arranging the plunger contact surface and at least part of the plunger within the body without coupling the plunger to the stopper, wherein
      i. the rod includes at least one rod shoulder directed away from the outlet end and the syringe includes a backstop arranged at a rear portion of the body, the backstop including a backstop shoulder directed towards the outlet end to cooperate with and contact the rod shoulder to prevent movement of the plunger away from the outlet end to a distance less than the length of the sterility zone, wherein when the plunger contact surface is in contact with the stopper the backstop shoulder and the rod shoulder are not in contact with one another,
      ii. ii) the syringe is dimensioned to have a nominal maximum fill volume of between 0.25 ml and 0.75 ml,
      iii. the variable volume chamber is filled with 40 mg/ml solution of aflibercept, and the dosage volume is 0.05 ml;
   c. enclosing and sealing the syringe into a package; and
   d. sterilizing the packaged syringe in a terminal sterilization process.

17. A method for treating an ocular disease in a subject in need thereof comprising administering to the subject an effective amount of aflibercept in a small volume, terminally sterilized syringe, wherein the syringe comprises
   a body, a stopper, and a plunger,
      wherein the body comprises an outlet at an outlet end and the stopper is arranged within the body such that a front surface of the stopper and the body define a variable volume chamber from which a fluid can be expelled though the outlet,
      wherein the stopper comprises at least a front circumferential rib and a rear circumferential rib which are separated in a direction along the longitudinal axis of the body to define a sterility zone having a length of at least 3 mm, wherein the plunger comprises a plunger contact surface at a first end and a rod extending between the plunger contact surface and a rear portion, the plunger contact surface is arranged to contact the stopper but does not couple thereto, such that the plunger can be used to force the stopper towards the outlet end of the body, thereby reducing the volume of the variable volume chamber, but does not to move the stopper away from the outlet end, whereby the syringe is suitable for ophthalmic injection, and wherein:

a) the rod includes at least one rod shoulder directed away from the outlet end and the syringe includes a backstop arranged at a rear portion of the body, the backstop including a backstop shoulder directed towards the outlet end to cooperate with and contact the rod shoulder to limit movement of the plunger rod away from the outlet end to a distance less than the length of the sterility zone, wherein when the plunger contact surface is in contact with the stopper the backstop shoulder and the rod shoulder are not in contact with one another, b) the syringe is dimensioned to have a nominal maximum fill volume of between 0.25 ml and 0.75 ml; and c) wherein the variable volume chamber is filled with 40 mg/ml solution of aflibercept, and the dosage volume is 0.05 ml.

18. The method of claim 17, wherein the ocular disease is selected from the group consisting of choroidal neovascularisation, age related macular degeneration, macular edema secondary to retinal vein occlusion (RVO), including both branch RVO (bRVO) and central RVO (cRVO), choroidal neovascularisation secondary to pathologic myopia (PM), diabetic macular edema (DME), diabetic retinopathy, and proliferative retinopathy.

19. The method of claim 17, wherein the variable volume chamber has an internal diameter between about 3 mm and about 6 mm.

20. The method of claim 17, wherein the length of the body of the syringe is less than 70 mm.

21. The method of claim 17, wherein the syringe is substantially silicone free.

22. The method of claim 17, wherein the body is made out of plastic or glass.

23. The method of claim 17, wherein the syringe is dimensioned so as to have a nominal maximum volume between about 0.4 ml and about 0.6 ml.

24. The method of claim 23, wherein the nominal maximum volume is about 0.5 ml.

25. The method of claim 17, wherein the syringe has an internal diameter between about 4.5 mm and about 4.8 mm.

26. The method of claim 17, wherein the outlet is reversibly sealed with a sealing device.

* * * * *